(12) United States Patent
Du

(10) Patent No.: US 8,513,259 B2
(45) Date of Patent: *Aug. 20, 2013

(54) NON-SEDATING ANTIHISTAMINE INJECTION FORMULATIONS AND METHODS OF USE THEREOF

(75) Inventor: Jie Du, Lansdale, PA (US)

(73) Assignee: JDP Therapeutics, Inc., Lansdale, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/238,453

(22) Filed: Sep. 21, 2011

(65) Prior Publication Data

US 2012/0010217 A1 Jan. 12, 2012

Related U.S. Application Data

(63) Continuation-in-part of application No. 12/829,857, filed on Jul. 2, 2010, now Pat. No. 8,314,083, which is a continuation-in-part of application No. 12/704,089, filed on Feb. 11, 2010, now Pat. No. 8,263,581.

(60) Provisional application No. 61/222,951, filed on Jul. 3, 2009, provisional application No. 61/248,441, filed on Oct. 3, 2009.

(51) Int. Cl.
*A61K 31/4965* (2006.01)

(52) U.S. Cl.
USPC .................................................. 514/255.04

(58) Field of Classification Search
None
See application file for complete search history.

(56) References Cited

U.S. PATENT DOCUMENTS

| | | | |
|---|---|---|---|
| 4,117,141 A | 9/1978 | Michaeli | |
| 4,434,237 A | 2/1984 | Dinarello | |
| 4,525,358 A | 6/1985 | Baltes et al. | |
| 4,826,689 A | 5/1989 | Violanto et al. | |
| 5,276,044 A | 1/1994 | Ambrus et al. | |
| 5,419,898 A | 5/1995 | Ikejiri et al. | |
| 5,492,935 A | 2/1996 | Yu et al. | |
| 5,627,183 A | 5/1997 | Gray | |
| 5,698,558 A | 12/1997 | Gray | |
| 6,258,816 B1 | 7/2001 | Singh et al. | |
| 6,319,927 B1 | 11/2001 | Martin | |
| 6,384,038 B1 | 5/2002 | Rubin | |
| 6,432,961 B1 | 8/2002 | Uylenbroeck et al. | |
| 6,451,815 B1 | 9/2002 | Hwang et al. | |
| 6,509,014 B1 | 1/2003 | De Lacharriere et al. | |
| 6,537,573 B2 | 3/2003 | Johnson et al. | |
| 6,660,301 B1 | 12/2003 | Vogel et al. | |
| 6,670,384 B2 | 12/2003 | Bandypadhyay et al. | |
| 6,720,001 B2 | 4/2004 | Chen et al. | |
| 6,790,847 B2 | 9/2004 | Walch | |
| 6,824,786 B2 | 11/2004 | Yu et al. | |
| 7,026,360 B1 | 4/2006 | Festo | |
| 7,115,563 B2 | 10/2006 | Younis et al. | |
| 7,338,657 B2 | 3/2008 | Vogel et al. | |
| 2001/0038863 A1 | 11/2001 | Jaenicke et al. | |
| 2002/0012700 A1 | 1/2002 | Johnson et al. | |
| 2002/0031558 A1 | 3/2002 | Yoo | |
| 2002/0048596 A1 | 4/2002 | Cevc | |
| 2002/0164374 A1 | 11/2002 | Jackson et al. | |
| 2002/0169190 A1 | 11/2002 | Bandyopadhyay et al. | |
| 2003/0068375 A1 | 4/2003 | Wright et al. | |
| 2003/0108496 A1 | 6/2003 | Yu et al. | |
| 2003/0134810 A1 | 7/2003 | Springate et al. | |
| 2003/0134811 A1 | 7/2003 | Jackson et al. | |
| 2003/0143184 A1 | 7/2003 | Seo et al. | |
| 2003/0144336 A1 | 7/2003 | Chen et al. | |
| 2003/0211083 A1 | 11/2003 | Vogel et al. | |
| 2004/0077540 A1 | 4/2004 | Quay | |
| 2004/0142852 A1 | 7/2004 | Younis et al. | |
| 2004/0185145 A1 | 9/2004 | Ehrman et al. | |
| 2004/0197324 A1 | 10/2004 | Liu et al. | |
| 2004/0203145 A1 | 10/2004 | Zamore et al. | |
| 2004/0228831 A1 | 11/2004 | Belinka, Jr. et al. | |
| 2004/0247660 A1 | 12/2004 | Singh | |
| 2004/0268425 A1 | 12/2004 | Bookbinder et al. | |
| 2005/0031667 A1 | 2/2005 | Patel et al. | |
| 2005/0031713 A1 | 2/2005 | Ehrich et al. | |
| 2005/0032173 A1 | 2/2005 | Rojas et al. | |
| 2005/0042293 A1 | 2/2005 | Jackson et al. | |
| 2005/0147607 A1 | 7/2005 | Reed | |
| 2005/0158408 A1 | 7/2005 | Yoo | |
| 2005/0202090 A1 | 9/2005 | Clarke | |
| 2005/0208134 A1 | 9/2005 | Magdassi et al. | |
| 2005/0260186 A1 | 11/2005 | Bookbinder et al. | |

(Continued)

FOREIGN PATENT DOCUMENTS

| EP | 1005865 A1 | 6/2000 |
|---|---|---|
| EP | 1109557 B1 | 11/2002 |

(Continued)

OTHER PUBLICATIONS

Aberg Declaration filed May 3, 2012 in parent U.S. Appl. No. 12/704,089.*
Hydroxyzine Description; American Regent Labortories, Inc.; 9 pages; Revised: Nov. 2006.
Linder et al.; ""Hydroxyzine Hemolysis in Surgical Patients"; Anesthesia and Analgesia"; 46(1); 6 pages; (1967).
"Hydroxyzine"; 2006 Lippincott's Nursing Drug Guide; ed. Lippincott Williams & Wilkins; http://web.sqe.edu.om/med-Lib/MED_CD/E_CDs/Nursing%20Drug%20Guide/mg/hydroxyzine.htm; (2006).
"Hydroxyzine (Atarax) Adverse Reactions"; RX-s.net Online pharmacy; http://rx-s.net/weblog/more/atarax_adverse_reactions/; last revised: Dec. 11, 2002.

(Continued)

Primary Examiner — Craig Ricci
(74) Attorney, Agent, or Firm — Cantor Colburn LLP

(57) ABSTRACT

Described herein are injectable compositions containing non-sedating or second and third generation antihistamines such as cetirizine/levocetirizine and methods of use thereof. Specifically, methods of treating acute urticaria or angioedema associated with an acute allergic reaction are disclosed. In certain embodiments, the injectable compositions are bioequivalent to currently marketed oral dosage forms with the same number of mg of cetirizine.

10 Claims, No Drawings

(56) References Cited

U.S. PATENT DOCUMENTS

| | | |
|---|---|---|
| 2005/0282879 A1 | 12/2005 | Salehani |
| 2006/0002963 A1 | 1/2006 | Rabinovich-Guilatt et al. |
| 2006/0079558 A1 | 4/2006 | Aberg et al. |
| 2006/0079559 A1 | 4/2006 | Aberg et al. |
| 2006/0079846 A1 | 4/2006 | Williams |
| 2006/0084683 A1 | 4/2006 | Uylenbroeck et al. |
| 2006/0095075 A1 | 5/2006 | Burkinshaw et al. |
| 2006/0104968 A1 | 5/2006 | Bookbinder et al. |
| 2006/0106364 A1 | 5/2006 | Whitlock et al. |
| 2006/0148903 A1 | 7/2006 | Burch et al. |
| 2006/0210604 A1 | 9/2006 | Dadey et al. |
| 2006/0211754 A1 | 9/2006 | Yu et al. |
| 2006/0216363 A1 | 9/2006 | Liu et al. |
| 2006/0241017 A1 | 10/2006 | Chandran |
| 2006/0247258 A1 | 11/2006 | Revirron |
| 2006/0287244 A1 | 12/2006 | Chandran |
| 2007/0014843 A1 | 1/2007 | Dobak |
| 2007/0020196 A1 | 1/2007 | Pipkin et al. |
| 2007/0021326 A1 | 1/2007 | Hamid et al. |
| 2007/0026058 A1 | 2/2007 | Pereswetoff-Morath et al. |
| 2007/0053900 A1 | 3/2007 | Liu et al. |
| 2007/0128276 A1 | 6/2007 | Jain et al. |
| 2007/0166368 A1 | 7/2007 | Singh |
| 2007/0191781 A1 | 8/2007 | Richards et al. |
| 2007/0203247 A1 | 8/2007 | Phillips et al. |
| 2007/0213660 A1 | 9/2007 | Richards et al. |
| 2007/0219498 A1 | 9/2007 | Malone et al. |
| 2007/0264349 A1 | 11/2007 | Lee et al. |
| 2007/0281947 A1 | 12/2007 | Matsumori |
| 2007/0286881 A1 | 12/2007 | Burkinshsw |
| 2008/0027030 A1 | 1/2008 | Stogniew et al. |
| 2008/0064721 A1 | 3/2008 | Rohrs et al. |
| 2008/0066741 A1 | 3/2008 | LeMahieu et al. |
| 2008/0103564 A1 | 5/2008 | Burkinshaw et al. |
| 2008/0145405 A1 | 6/2008 | Kunzler et al. |
| 2008/0145419 A1 | 6/2008 | Gibson et al. |
| 2008/0152708 A1 | 6/2008 | Gibson et al. |
| 2008/0214649 A1 | 9/2008 | Yu et al. |
| 2008/0294261 A1 | 11/2008 | Pauza et al. |
| 2008/0311171 A1 | 12/2008 | Patel et al. |
| 2009/0010924 A1 | 1/2009 | Wu et al. |
| 2009/0048268 A1 | 2/2009 | Asotra et al. |
| 2009/0054994 A1 | 2/2009 | Rogan et al. |
| 2009/0123367 A1 | 5/2009 | Bookbinder et al. |
| 2009/0137606 A1 | 5/2009 | Cohen |
| 2009/0156504 A1 | 6/2009 | Siegel et al. |
| 2009/0181908 A1 | 7/2009 | Kaspar et al. |
| 2009/0186038 A1 | 7/2009 | Reed |
| 2009/0216183 A1 | 8/2009 | Minotti |
| 2009/0227564 A1 | 9/2009 | Sugamata |
| 2009/0280129 A1 | 11/2009 | Liu et al. |
| 2009/0298869 A1 | 12/2009 | Burnier et al. |
| 2009/0304648 A1 | 12/2009 | Owen |
| 2009/0311311 A1 | 12/2009 | Shantha et al. |
| 2009/0312766 A1 | 12/2009 | Shantha et al. |
| 2010/0008996 A1 | 1/2010 | Meinert |
| 2010/0022496 A1 | 1/2010 | Perovitch et al. |
| 2010/0029662 A1 | 2/2010 | Horn |
| 2010/0069402 A1 | 3/2010 | Melamed |
| 2011/0004164 A1 | 1/2011 | Du |
| 2011/0008325 A1 | 1/2011 | Pipkin et al. |
| 2012/0053563 A1 | 3/2012 | Du |

FOREIGN PATENT DOCUMENTS

| | | |
|---|---|---|
| EP | 1098870 B1 | 10/2005 |
| WO | WO 98/00159 A1 | 1/1998 |
| WO | WO 98/22130 A1 | 5/1998 |
| WO | WO 00/06531 A2 | 2/2000 |
| WO | WO 01/28555 A1 | 4/2001 |
| WO | WO 02/47689 A2 | 6/2002 |
| WO | 02067938 A2 | 9/2002 |
| WO | WO 2004/084865 A1 | 10/2004 |
| WO | 2006047427 | 5/2006 |
| WO | WO 2009/044141 A1 | 4/2009 |

OTHER PUBLICATIONS

Shands "Drugs & Therapy Bulletin"; 15(6) 4 pages; (2001).
Tokodi, Jr., et al.; "Massive Tissue Necrosis After Hydroxyzine Injection"; J. Am Osteopath Assoc; 95(10); p. 609; Abstract only; (1995).
Krause, Richard S.; "Anaphylaxis"; eMedicine.com, Updated: Oct. 6, 2008.
Salzberg, et al.; "Anaphylaxis: When Seconds Count"; Emerg Med 39(5):18; 7 pages (2007).
Sampson, et al.; "Symposium on the Definition and Management of Anaphylaxis: Summary Report"; J Allergy Clin Immunol; 115; pp. 584-591; (2005).
Linzer, Jeffrey F. Sr.; "Pediatrics, Anaphylaxis"; eMedicine.com; 9 pages; Updated: Jan. 10, 2008.
Sampson, Hugh A.; "Anaphylaxis and Emergency Treatment"; Pediatrics; 111(6): pp. 1601-1608; (2004).
Zyrtec-D 12 Hour (cetirizine hydrochloride 5 mg and pseudoephedrine hydrochloride 120 mg) Extended Release Tablets; product label; Pfizer Labs; Marketed by UCB Pharma, Inc.; 13 pages; Revised Aug. 2003.
Xyzal (levocetirizine dihydrochloride) 5 mg tablets; product label; UCB, Inc., 9 pages; (2009).
Allegra (fexofenadine hydrochloride) tablets; product label; Allegra ODT manufactured for sanofi-aventis U.S. LLC; 19 pages; (2007).
Epipen (epinephrine) Auto-Injector 0.3 mg; label; Meridian Medical Technologies, Inc., Manufactured for Dey, L.P. 7 pages; (Sep. 2008).
International Search Report and Written Opinion; International Application No. PCT/US10/40925; International Filing date Jul. 2, 2010; date of Mailing Aug. 30, 2010; 12 pages.
Pfizer Labs, Zyrtec; May 1, 2006, online drug review, retrieved Mar. 28, 2011, from pfizer.com/files/products/uspi_syrtec.pdf, 14 pages.
Tillement et al., "Compared Pharmacological Characteristics in Humans of Racemic Cetirizine and Levocetirizine, Two Histamine H1-Receptor Antagonists"; Biochemical Pharmacology; 66; No, 7; pp. 1123-1126; (2003).
Allegra (fexofenadine hydrochloride) tablets; product label; Allegra ODT manufactured for sanofi-aventis U.S. LLC; 19 pages, 2007.
Banerji et al. "Diphenhydramine versus nonsedating antihistamines for acute allergic reactions: A literature review" Jul.-Aug. 2007, *Allergy and Asthma Proceedings* 28(4):418-426.
Coyle et al. "The effect of cetirizine on antigen-dependent leucopenia in the guinea-pig" Jun. 1991, *Br. J. Pharmacol.* 103(2):1520-1524.
Desager et al. "A pharmacokinetic evaluation of the second-generation H1-receptor antagonist cetirizine in very young children" Apr. 1993, *Clin. Pharmacol. Ther*. 53(4):431-435.
Dux et al. "Possible role of histamine (H1- and H2-) receptors in the regulation of meningeal blood flow" Nov. 2002, *Br. J. Pharmacol.* 137(6):874-880.
Epipen (epinephrine) Auto-Injector 0.3 mg; label; *Meridian Medical Technologies, Inc., Manufactured for Dey L.P.*, 7 pages, Sep. 2008.
International Search Report and Written Opinion dated Aug. 30, 2010 for PCT/U52010/040925.
Jaber et al. "Determination of cetirizine dihydrochloride, related impurities and preservatives in oral solution and tablet dosage forms using HPLC" Oct. 29, 2004, *J. Pharm, Biomed. Anal*. 36(2):341-350.
Krause "Anaphylaxis" updated Sep. 2, 2009, eMedicine.com.
Lieberman "The use of antihistamines in the prevention and treatment of anaphylaxis and anaphylactoid reactions" Oct. 1990, *J. Allergy Clin. Immunol.* 86(4/2):684-686.
Linzer Sr. "Pediatrics, Anaphylaxis" updated Mar. 29, 2011, eMedicine.com, 9 pages (TOC).
Salzberg et al. "Anaphylaxis: When Seconds Count" 2007, *Emerg. Med*. 39(5):18-24.
Sampson "Anaphylaxis and Emergency Treatment" 2004, *Pediatrics* 111(6):1601-1608.
Sampson et al. "Symposium on the Definition and Management of Anaphylaxis: Summary Report" 2005, *J. Allergy Clin. Immunol.* 115(3):584-591.
Xyzal (levocetirizine dihydrochloride) 5 mg. tablets; product label; *UCB, Inc.*; 9 pages, 2009.

Zyrtec-D 12 Hour (Cetirizine Hydrochloride 5 mg and Pseudoephedrine Hydrochloride 120 mg) Extended Release Tablets; product label; *Pfizer labs; Marketed by UCB Pharma, Inc.*, 12 pages; revised Aug. 2003.

U.S. Appl. No. 12/704,089, filed Feb. 11, 2010, NonFinal Office Action of Aug. 5, 2011, 19 pages.

Annals of Allergy, Asthma & Immunology; 85; pp. 525-531; (2000).

"Metoclopramide Injection", Solution (archived drug label, Jun. 2006; available online at http://dailymed.nlm.nih.gov).

U.S. Appl. No. 12/829,857, filed Jul. 2, 2010, NonFinal Office Action of Mar. 15, 2012, 24 pages.

Winbery, et al.; "Histamine and antihistamines an anaphylaxis" Clin Allergy Immunol; 17; pp. 287-317; Abstract only (2002).

EPO Search Report; Application No. PCT/US/2010040925; date of completion Oct. 17, 2012; 8 pages.

Jones et al.; "Time-dependent Inhibition of Histamine-Induced Cutaneous Responses by Oral and Intramuscular Diphenhydramine and Oral Fexofenadine"; Annals of Allergy, Asthma & Immunology; 100; pp. 452-456; (2008).

U.S. Appl. No. 13/291,514, filed Nov. 8, 2011 NonFinal Office Action Mailed Aug. 31, 2012, 29 pages, (IFW).

\* cited by examiner

NON-SEDATING ANTIHISTAMINE INJECTION FORMULATIONS AND METHODS OF USE THEREOF

CROSS REFERENCE TO RELATED APPLICATION

This application is continuation in part of U.S. application Ser. No. 12/829,857 filed on Jul. 2, 2010, which is a continuation in part of U.S. application Ser. No. 12/704,089 filed on Feb. 11, 2010, which is a nonprovisional of U.S. Provisional Application Ser. Nos. 61/248,441 filed Oct. 3, 2009 and 61/222,951 filed Jul. 3, 2009, all which are hereby incorporated by reference in their entirety.

BACKGROUND

Acute allergic reaction, ranging from the milder cases of acute urticaria to the most severe cases of anaphylaxis, is a systemic, immediate hypersensitivity reaction caused by exposure to a specific antigen. The immune system activates immunoglobulin E (IgE), which reacts with effector cells (mast cells and basophils). These cells, in turn, release histamine, serotonin, leukotrienes, and prostaglandins, and induce a range of signs and symptoms, such as facial flushing, acute urticaria, edema, pruritus, broncho-constriction, cough, cardiac arrhythmias, hypotension, nausea, vomiting, and diarrhea. Cutaneous manifestations are most common, with acute urticaria and angioedema present in 88% or more of patients experiencing acute allergic reactions. Swelling in the airway, a part of anaphylaxis, is the most life-threatening symptom, commonly causing dyspnea, wheezing, stridor, and upper airway obstruction from severe edema. Cardiovascular symptoms associated with anaphylaxis include dizziness, hypotension, and syncope related to third-spacing of intravascular fluid. Common gastrointestinal manifestations include nausea, vomiting, abdominal pains or cramps, and diarrhea. Although symptoms vary between acute allergy patients, onset generally occurs seconds to minutes after exposure to an antigen and requires prompt treatment.

The true incidence of acute allergic reactions is unknown, partly because of the lack of a precise definition of the syndrome. Some clinicians reserve the term anaphylaxis for the full-blown syndrome, while others use it to describe milder cases. Fatal anaphylaxis is relatively rare; milder forms occur much more frequently. The frequency of acute allergic reaction is increasing, and this has been attributed to the increased number of potential allergens to which people are exposed, such as increased varieties of food and medications. A recent review concluded that the lifetime prevalence of acute allergic reactions including anaphylaxis is approximately 5% of the population, with a higher prevalence in developed countries than developing countries.

Approximately 1 in 5000 exposures to a parenteral dose of a penicillin or cephalosporin antibiotic causes anaphylaxis. More than 100 deaths per year are reported in the United States due to antibiotic induced allergies. Fewer than 100 fatal reactions to Hymenoptera stings are reported each year in the United States but this is considered to be an underestimate. One to 2% of people receiving IV radiocontrast experience some sort of reaction. The majority of these reactions are minor, and fatalities are rare. Low molecular weight contrast causes fewer and less severe reactions. Narcotics also induce acute allergic reactions.

Acute allergic reactions occur in all age groups. Food allergies are more common in the young, whereas more drug reactions occur in adults, possibly due to greater exposure to medications, including narcotics, aspirin/NSAIDs, antibiotics, IV contrast media, anesthesia, muscle relaxants, etc. Although prior exposure is essential for the development of true anaphylaxis, reactions occur even when no documented prior exposure exists. Thus, patients may react to a first exposure to an antibiotic or insect sting. Elderly persons have the greatest risk of mortality from acute allergic reactions due to the presence of preexisting disease.

Emergency treatment for acute allergic reactions includes airway protection, alpha-agonists, antihistamines, steroids, and beta agonists. Medications currently used in the treatment of acute allergic reactions include epinephrine, diphenhydramine injection, corticosteroids, albuterol, and glucagon. Epinephrine is the first-line drug to be given to a patient having an acute allergic reaction including anaphylaxis. Where breathing issues or airway constriction is an issue, epinephrine should remain the first-line drug. The first generation antihistamine (injectable diphenhydramine) is used as the second-line drug to be given to a patient having an acute allergic reaction as an adjunct therapy to epinephrine for the relief of peripheral symptoms such as pruritus, angioedema, acute urticaria, erythema, wheezing, etc. An alpha-receptor agonist, epinephrine reverses hypotension. It also has beta-receptor activity, which dilates the airways, increases the force of myocardial contraction, and suppresses histamine and leukotriene release, reducing inflammatory responses. Where airway constriction or breathing issues are being controlled or are not concerned, first generation antihistamine such as an injectable diphenhydramine injection may be used alone without epinephrine.

The current treatment with diphenhydramine injection suffers from several drawbacks, including its short half-life, its highly sedative nature, the large number of potential drug/drug interactions, the potential cardiotoxicity (QT prolongation), and other potential side effects. Accordingly, new treatments for acute allergic reactions are needed, particularly for use in the emergency setting.

SUMMARY

In one aspect, a method of increasing peak plasma concentration and/or providing immediate onset of plasma concentration of cetirizine in an individual in need of treatment for acute urticaria or angioedema associated with an acute allergic reaction, wherein the acute allergic reaction optionally includes anaphylaxis comprises administering to the individual an intravenous injection of an injectable cetirizine composition containing 2 mg to 20 mg of cetirizine at a rate of 10 mg per 1.0-1.5 minutes or faster, wherein the peak plasma concentration (Cmax) of the intravenous injectable cetirizine composition is greater than twice the Cmax of a reference immediate-release oral cetirizine dosage form having the same number of mg of cetirizine as the injectable cetirizine composition, and wherein the and area under the plasma time curve measured as $AUC_{0-36hr}$ and $AUC_{0-inf}$ is substantially the same for the intravenously injectable cetirizine composition and the reference immediate-release oral cetirizine dosage form.

In another aspect, a method of decreasing the time for cetirizine to appear in the bloodstream of a patient in need of treatment for acute urticaria or angioedema associated with an acute allergic reaction, wherein the acute allergic reaction optionally includes anaphylaxis comprises administering to the patient an intramuscular injection of an injectable cetirizine composition containing 2 mg to 20 mg of cetirizine, wherein at least about 5 ng/mL of cetirizine appears in the patient's bloodstream within about 4 minutes of administration.

In yet another aspect, a method of treating a patient in need of injection with cetirizine comprises administering to the patient an intravenous injection of an injectable cetirizine composition containing 2 mg to 20 mg of cetirizine at a rate of 10 mg per 1.0-1.5 minutes or faster, to provide an immediate about 2 minute peak plasma concentration (Cmax) of the intravenous injectable cetirizine composition that is greater than twice the Cmax of a reference immediate-release oral cetirizine dosage form having the same number of mg of cetirizine as the injectable cetirizine composition, or administering an intramuscular injection of an injectable cetirizine composition containing 2 mg to 20 mg of cetirizine, wherein at least about 5 ng/mL of cetirizine appears in the patient's bloodstream within about 4 minutes of administration.

In yet another aspect, an injectable composition comprises 2 to 20 mg of cetirizine per mL, 1 to 9 mg of sodium chloride per mL, 2 to 20 mg of benzyl alcohol per mL, and water q.s. to 100%, adjusted to a pH of about 5.5+/−1.0.

DETAILED DESCRIPTION

Prior to the work of the present inventor, injectable cetirizine had never been formulated or tested as a treatment for a disease in a human or other mammal. In the study presented herein, for the first time, both intravenous and intramuscular cetirizine injection were administered to 24 human volunteers in a phase I clinical study. Pharmacokinetic modeling projected that the Cmax for intravenous administration of cetirizine would be 1.7 times that of the oral administration of the same number of mg of cetirizine. However this study unexpectedly shows that intravenous injection of cetirizine can increase the peak plasma concentration by about 4.2 times compared to administration of the oral tablet and/or provides immediate onset of plasma concentration of cetirizine within 2 minutes. As used herein, immediate onset means that cetirizine reaches its peak concentration (Cmax) within about 2 minutes of administration of the dosage form. It was also unexpectedly shown that the Cmax for the intravenous cetirizine injection is about 7.7 times that of the Cmax for the intramuscular injection, but with the same AUC. In addition, the data also unexpectedly shows that intramuscular injection of cetirizine decreased Cmax by about 45% compared to the oral tablet, but provided nearly immediate drug appearance in blood stream in about 4 minutes. This pharmacokinetic profile is particularly advantageous for treatment of individuals in need of treatment for acute urticaria or angioedema associated with an acute allergic reaction, wherein the acute allergic reaction optionally includes anaphylaxis.

Also as used herein, a patient or individual means a human or another mammal.

It was reported in the Cetirizine Tablet (Zyrtec®) Product Insert that the cetirizine oral tablet has a bioavailability of about 70%. From this data, one would estimate that the AUC of a cetirizine IV injection is about 30% higher than the AUC of the oral tablet with the same number of mg of cetirizine. However, it was unexpectedly discovered in the clinical trials presented herein that the AUC for administration of the IV dosage is equivalent to the AUC for administration of the tablet with the same mg of cetirizine.

In one embodiment, a method of increasing the peak plasma concentration and/or providing immediate onset of plasma concentration of cetirizine in an individual in need of treatment for acute urticaria or angioedema associated with an acute allergic reaction, wherein the acute allergic reaction optionally includes anaphylaxis, comprises administering to the individual an intravenous injection of an injectable cetirizine composition containing 2 mg to 20 mg of cetirizine at a rate of 10 mg per 1.0-1.5 minutes or faster, wherein the peak plasma concentration (Cmax) of the intravenous injectable cetirizine composition is greater than twice the Cmax of a reference immediate-release oral cetirizine dosage form having the same number of mg of cetirizine as the injectable cetirizine composition, and wherein the area under the plasma time curve measured as $AUC_{0-36hr}$ and $AUC_{0-inf}$ is substantially the same for the intravenously injectable cetirizine composition and the reference immediate-release oral cetirizine dosage form. In one embodiment, cetirizine is the only active agent in the injectable composition.

As used herein, an immediate-release oral dosage form comprises no added release-retarding excipients to extend the rate of release. The commercially available Zyrtec® (cetirizine) 10 mg tablet is an immediate-release dosage form.

In one embodiment, the peak plasma concentration (Cmax) of the intravenous injectable cetirizine composition is about 4.2 times that of the Cmax of a reference oral cetirizine dosage form. As used herein, about 4.2 times that of the Cmax of a reference oral cetirizine dosage form means that the Cmax is between 3 and 5.5 times that of the reference dosage form. In one embodiment, the mean Cmax for a 10 mg reference oral cetirizine dosage form is about 318 ng/ml and the mean Cmax for a 10 mg injectable formulation via IV is about 1345 ng/ml hr. In another embodiment, the mean $AUC_{0-36}$ for a 10 mg reference oral cetirizine dosage form and a 10 mg injectable formulation via IV or IM is about 2550-2640 ng/ml hr, and the mean $AUC_{0-INF}$ is about 2650-2772 ng/ml hr.

In certain embodiments, administration by intravenous (IV) injection or intramuscular (IM) injection does not significantly increase side effects such as drowsiness and dry mouth compared to oral administration of a reference oral cetirizine dosage form.

In another aspect, a method of treating a patient in need of injection with cetirizine comprises administering to the patient an intravenous injection of an injectable cetirizine composition containing 2 mg to 20 mg of cetirizine at a rate of 10 mg per 1.0-1.5 minutes or faster, to provide an immediate about 2 minute peak plasma concentration (Cmax) of the intravenous injectable cetirizine composition that is greater than twice the Cmax of a reference immediate-release oral cetirizine dosage form having the same number of mg of cetirizine as the injectable cetirizine composition, or administering an intramuscular injection of an injectable cetirizine composition containing 2 mg to 20 mg of cetirizine, wherein at least about 5 ng/mL of cetirizine appears in the patient's bloodstream within about 4 minutes of administration. Patients include those who in need of treatment for acute urticaria or angioedema associated with an acute allergic reaction, wherein the acute allergic reaction optionally includes anaphylaxis, and/or patients who are unable to take oral cetirizine. As used herein, about 2 minutes means 1 to 3 minutes. In one embodiment, cetirizine is the only active agent in the injectable composition.

In the embodiment of an intravenous injection, the peak plasma concentration (Cmax) of the intravenous injectable cetirizine composition may be greater than twice the Cmax of a reference immediate-release oral cetirizine dosage form having the same number of mg of cetirizine as the injectable cetirizine composition, and wherein the area under the plasma time curve measured as $AUC_{0-36hr}$ and $AUC_{0-inf}$ is substantially the same for the intravenously injectable cetirizine composition and the reference immediate-release oral cetirizine dosage form; where the injectable cetirizine composition is injected at a rate of 10 mg per 1.0-1.5 minutes or faster. In another embodiment, the peak plasma concentration (Cmax) of the intravenous injectable cetirizine composition is about 4.2 times that of the Cmax of a reference oral cetirizine dosage form.

In the embodiment of an intravenous injection, the area under the plasma time curve measured as $AUC_{0-1hr}$ for the intravenous injection may be about twice as large as the the $AUC_{0-1hr}$ for a reference immediate-release oral cetirizine dosage form having the same number of mg of cetirizine as the injectable cetirizine composition. In another embodiment, the area under the plasma time curve measured as $AUC_{0-2hr}$ for the intravenous injection is at about 1.5 times as large as the $AUC_{0-2hr}$ for a reference immediate-release oral cetirizine dosage form having the same number of mg of cetirizine as the injectable cetirizine composition.

In another embodiment, a method of decreasing the time for cetirizine to appear in the bloodstream of a patient in need of treatment for acute urticaria or angioedema associated with an acute allergic reaction, wherein the acute allergic reaction optionally includes anaphylaxis, comprises administering to the patient an intramuscular injection of an injectable cetirizine composition containing 2 mg to 20 mg of cetirizine, wherein at least about 5 ng/mL of cetirizine starts to appear in the patient's bloodstream within about 4 minutes of administration. As used herein, about 4 minutes means 3 to 5 minutes.

Acute allergic reaction, optionally including anaphylaxis, is an acute multi-system severe type I hypersensitivity reaction. Pseudoanaphylaxis does not involve an allergic reaction, but is due to direct mast cell degranulation. Both anaphylaxis and pseudoanaphylaxis result in an anaphylactoid reaction and treatment for both conditions is similar. The term anaphylaxis as used herein refers to both conditions unless otherwise specified. Clinical signs and symptoms of acute allergic reaction are given in Table 1:

TABLE 1

Clinical signs and symptoms of acute allergic reactions optionally including anaphylaxis Cutaneous/subcutaneous/mucosal tissue Flushing, pruritus, acute urticaria, angioedema, morbilliform rash, pilor erection
Pruritus of lips, tongue, and palate; edema of lips, tongue, and uvula
Periorbital pruritus, erythema and edema, conjunctival erythema, tearing
Respiratory Laryngeal: pruritus and tightness in the throat, dysphagia, dysphonia and hoarseness, dry staccato cough, stridor, sensation of pruritus in the external auditory canals
Lung: shortness of breath, dyspnea, chest tightness, deep cough and wheezing/bronchospasm (decreased peak expiratory flow)
Nose: pruritus, congestion, rhinorrhea, sneezing
Cardiovascular Hypotension
Feeling of faintness (near-syncope), syncope, altered mental status
Chest pain, dysrhythmia
Gastrointestinal Nausea, crampy abdominal pain, vomiting (stringy mucus), diarrhea
Other Uterine contractions in women, and aura of doom Disclosed herein are injection formulations of non-sedating antihistamines to be used, for example, in the hospital or acute care settings, for the treatment of acute allergic reactions or symptoms (acute urticaria, angioedema, etc) associated with them. In acute allergic reactions, an antigen interacts with and cross-links surface IgE antibodies on mast cells and basophils. Once the mast-cell-antibody-antigen complex is formed, a complicated series of events occurs that eventually leads to mast cell degranulation and the release of histamine and other chemical mediators from the mast cell or basophil. After its release, histamine can react with local or widespread tissues through histamine receptors. Histamine receptor sites, histamine-1 ($H_1$), and histamine-2 ($H_2$) have a role in acute allergic reactions/anaphylaxis. Acting on $H_1$ receptors, histamine produces pruritus, vasodilation, hypotension, flushing, headache, tachycardia, bronchoconstriction, and increased vascular permeability. Targeting $H_2$-receptor sites, histamine causes increased stomach acid production, nausea, and flushing.

Symptoms of acute allergic reactions include pruritus, erythema, angioedema, acute urticaria, urticaria areas, erythema areas, wheezing, and etc. In one embodiment, an acute allergic reaction is characterized by acute urticaria or angioedema. Exemplary patient populations for study include patients coming to emergency rooms or allergy clinics, patients with food allergies (peanuts, other nuts, sea food, etc), patients with exercise induced allergies, patients allergic to insects stings, patients with poison Ivy induced allergies, etc. Additional patients include those already in the hospital experiencing drug induced allergies to: antibiotics (e.g., penicillin), IV contrast media, anesthesia, aspirin/NSAIDs, opioids, chemotherapy agents, muscle relaxants, latex gloves, blood materials, etc.

Oral cetirizine formulations are available for treatment of seasonal and perennial rhinitis and chronic idiopathic urticaria. Cetirizine has never been tested or approved for use in treating symptoms (acute urticaria, angioedema, etc.) associated with acute allergic reaction (optionally including anaphylaxis) nor proposed for injectable use. Several known factors have prevented scientists from trying to make cetirizine, its salts, polymorphs, and its isomers (i.e., levocetirizine) into a parenteral injection product for the treatment and/or prevention of acute allergic reactions or symptoms associated with acute allergic reactions optionally including anaphylaxis. These factors are:

i) Key opinion leaders in the allergy space have published articles about $2^{nd}/3^{rd}$ generation antihistamines being unfeasible to make into an injection product. For example, Dr. Phillip Liberman, a world renowned allergist, published an article specifying that non-sedating antihistamines are not able to be given by the traditionally employed injectable route, due to in-solubility.

ii) Cetirizine, its salts or its isomer levocetirizine is a newer-generation ($2^{nd}$ or $3^{rd}$ generation) antihistamine and a metabolite of the first-generation antihistamine hydroxyzine. As such, cetirizine and its isomers and hydroxyzine are similar in structure. The injectable product of cetirizine's parent molecule, hydroxyzine, is known to cause hemolysis when injected intravenously due to its serious hemolytic effects. In fact, the FDA requires a label on hydroxyzine injection indicating that the injectable product can not be given intravenously. As a result, it has been generally thought that as a metabolite of hydroxyzine, cetirizine, and/or levocetirizine, its salts or isomers would have similar hemolytic problem as the parent compound, thus would not be suitable as an injection product for intravenous administration.

iii) The current treatment for acute allergic reaction is to use the $1^{st}$ generation antihistamine diphenhydramine injection which has been on the market as the treatment standard for approximately 60 years. Specifically, diphenhydramine has been considered the "gold standard" for the treatment of acute allergic reactions, and it was thought that newer generation of antihistamines are not as effective. Its heavy sedation side effects were often considered advantageous sometimes for acute allergic reactions by calming and relaxing the patients, especially the pediatric patents, since many patients with this condition are children. Only the first generation antihistamines have such a sedation side effect.

iv) Due to the severity of acute allergic reactions, scientists believed nothing but diphenhydramine was strong enough in efficacy to treat acute allergic reactions. When formulating second and third generation antihistamines products, scientists added an anti-inflammatory agent to the formulation to aid the antihistamine effect even for chronic allergies. Singh et al. disclosed a combination injectable formulation of cetirizine with an anti-inflammatory agent, nimesulide (an NSAID), for allergic disorders namely rhinitis, bronchitis, asthma, urticaria and the like, all of which are chronic allergies.

These factors may have prevented scientists from trying to make cetirizine, its salts, polymorphs, and its isomers (i.e. levocetirizine) into a parenteral injection product for the treatment and/or prevention of acute allergic reactions or symptoms (acute urticaria, angioedema, etc.) associated with acute allergic reactions, optionally including anaphylaxis. The old diphenhydramine injection has been the only antihistamine injections available in the last 60 years for the treatment of acute allergic reactions optionally including anaphylaxis, or symptoms (acute urticaria, angioedema, etc.) associated with acute allergic reactions, optionally including anaphylaxis.

Surprisingly, the inventor has discovered and successfully formulated cetirizine into a parenteral injection product, particularly for IV injection. The unique cetirizine injectable formulation disclosed herein is substantially free of the hemolytic effect seen in its parent compound hydroxyzine. The cetirizine formulations and methods of treatment disclosed herein are effective in treating acute allergic reaction or symptoms (acute urticaria, angioedema, pruritus, erythema, wheezing, or combination thereof) associated with acute allergic reaction in the absence of an NSAID, and without sedating effect of the existing gold-standard treatments.

With respect to sedative effect, injections of cetirizine and its pharmaceutically acceptable salts, isomers (e.g., levocetirizine), or polymorphs, have significantly reduced sedative effects when compared to the first generation antihistamines, hydroxyzine IM injection and diphenhydramine injection. In the effective dose range and particularly at a proposed 10 mg daily dose, cetirizine injection is substantially free of sedative effect when compared to hydroxyzine IM injections and/or diphenhydramine injection. The sedative-free effect permits administration of cetirizine injection to specific populations of patients. As discussed herein, cetirizine injectable formulations, or injections of its salts, isomers (i.e., levocetirizine) and polymorphs, can be given to patients with reduced sedation, reduced fear of drug/drug interactions, reduced fear of hemolytic potential, reduced frequency of drug administration, reduced fear of additive sedative effects, reduced fear of cardiotoxicity (QT prolongation), and with reduced monitoring efforts and requirements, when compared to diphenhydramine injections.

Acute urticaria is an acute allergic reaction related to the skin and subcutaneous tissues. It is a vascular reaction of the upper dermis marked by transient, slightly elevated patches called wheals that are redder or paler than the surrounding skin; there often is severe itching. Acute urticaria may arise from a food allergy (e.g., peanuts), drug allergy (e.g., penicillin), insect sting (venom), or the like, and it is distinct from chronic urticaria (or chronic idiopathic urticaria, or urticaria) which is recurrent, spontaneous, and lasts for longer than 6 weeks to year long, and can rarely be associated with a specific cause. Chronic urticaria is also called Chronic Idiopathic Urticaria, or simply Urticaria. Chronic urticaria is defined as urticaria with recurrent episodes lasting longer than 6 weeks, caused by unknown reasons or no reason. Acute urticaria is short in duration; and the eruption rarely lasts more than several days. Acute urticaria is associated with acute allergic reactions, and many of them are life-threatening angioedema and/or anaphylactic shock, such as allergic shock to peanuts, penicillin, etc. Due to the urgency and the acute condition of this disease that seconds count, oral medication may not be feasible for the treatment because oral medication may take too long to have an onset of action. Therefore there is a need to develop an injectable product for the treatment of acute allergic reactions or symptoms (acute urticaria, angioedema, etc.) associated with acute allergic reaction optionally including anaphylaxis in a human or other mammal. However, there have been no drugs developed in the last 60 years for the treatment of acute allergic reaction or acute urticaria, angioedema associated with acute allergic reaction optionally including anaphylaxis.

Cetirizine as currently marketed does not exist in an injectable form, and never was tested for the treatment of symptoms (acute urticaria, angioedema, etc.) associated with acute allergic reactions optionally including anaphylaxis, because cetirizine was thought not feasible as an IV injection for the reasons described above. Described herein are methods of treating acute urticaria and angioedema associated with an acute allergic reaction, wherein the acute allergic reaction optionally includes anaphylaxis, using a cetirizine injection.

Pruritus associated with acute allergic reaction is a condition involving localized or general itching that is a common and distressing symptom in a variety of diseases, especially in an acute allergic reaction. Although usually occurring in the skin, pruritus can also occur in non-cutaneous sites such as mucous membranes. Erythema associated with acute allergic reaction is redness of the skin, caused by congestion of the capillaries in the lower layers of the skin. The primary efficacy endpoints included the pruritus severity score and the erythema severity score (scored on a 0=absent, 1=mild, 2=moderate, to 3=severe scale, at 0.5 increments), and the reduction of the scores following treatment. For clinical trials, patients with "score 1-3" (mild to severe) will be recruited.

The primary efficacy end points are the difference between the treatment disclosed herein and the treatment of placebo in the mean change from the baseline of the average of the pruritus severity score and the erythema severity score. The study will be designed to give a 90% power to detect a 0.5 unit mean difference for the primary efficacy endpoint at a two-sided alpha-level of 0.05.

Angioedema associated with acute allergic reaction is an uncomfortable and disfiguring type of temporary swelling especially in the lips and other parts of the mouth and throat, the eyelids, the genitals, and the hand and feet. Angioedema is life-threatening if swelling in the mouth or throat makes it difficult to breathe. Less often the sheer amount of swelling means that so much fluid has moved out of the blood circulation that blood pressure drops dangerously. The primary efficacy endpoints for angioedema include the angioedema severity score (scored on a 0=absent, 1=mild, 2=moderate, to 3=severe scale, at 0.5 increments), and the reduction of the score following treatment.

Exemplary clinical studies include a randomized, double-blind, active and placebo—controlled trial of about 300 patients over the age of 12 with acute allergic reactions. About 100 patients will be randomly assigned to each of the 3 treatments including a non-sedating antihistamine injection as disclosed herein, a diphenhydramine injection, or a placebo injection, all via intravenous, intramuscular or subcutaneous administration. Patients will be recruited at multiple centers, from hospitals, emergency departments, and allergy clinics throughout the country. The primary endpoints will be the reduction of pruritus severity score, pruritus duration, erythema, angioedema, wheezing, number of urticaria, area of urticaria, and/or number of erythema areas, at 2-4 hours after protocol treatment. Symptom scores will be also assessed at baseline.

A broad definition of allergic reactions to approximate real-life emergency department (ED) approaches will be used to assess the patients with various symptoms and signs. Patients over the age of 12 will be considered for recruitment from the ED if they have the following symptoms after an ingested food or ingested, inhaled, or injected drug, after in contact with latex or bee stings: acute urticaria (score 1 and above), acute angioedema (score 1 and above), wheezing (score 1 and above), and acute pruritic rash (score 1 and above). These manifestations should have been present for no greater than 12 hours from the time of alleged allergen exposure. Pregnant patients will be excluded. Recruited patients will be randomly assigned to treatment with either 10 mg of cetirizine injection (the test product group, i.e. product of present disclosure), diphenhydramine 50 mg injection (the comparator or active control group) or placebo injection (placebo control group)

Each treatment designation will be blinded based on the randomization code. The physician who is unaware of the treatment content will administer the contents by means of intravenous (or intramuscular, or subcutaneous, depending on protocol requirement) injection to the subject. Supplemental medications, such as epinephrine, corticosteroids, bronchodilators, and additional doses of antihistamine may be administered at the discretion of the study physicians as a rescue procedure. Patients may also receive supplemental oxygen and intravenous fluids at the discretion of the study physicians as a rescue procedure. Patients will have heart rate, blood pressure, physical findings, side effects, and symptoms assessed at baseline, 1 hour, 2 hours and 4 hours relative to experimental treatment. Baseline temperatures will be also recorded. Clinical recording will include the presence and extent or severity scores of the acute urticaria and erythema, angioedema, wheezing, pruritus, number/size of urticaria areas, number/size of erythema areas, abdominal distention or tenderness, and abdominal hyperactive bowel sounds. Historical features, physical findings (including heart rates, blood pressure, and respiratory rates), and treatments will be recorded on a study-specific data input form. The extent of involvement with acute urticaria and erythema will be assessed by using a check-off cartoon of body areas (similar to that used to assess burn area extent) printed on the data input sheet. Symptom scores will be assessed at baseline, 1 hour, and 2, or 4 hours by using a preprinted form with none (score 0), mild (score 1), moderate (score 2), and severe (score 3) check-off categories.

The primary variables of interest will be resolution or reduction of acute urticaria, angioedema, erythema, pruritus, wheezing, number/size of urticaria areas, and number/size of erythema areas. Changes in heart rates, respiratory rates, blood pressure, and symptoms will also be examined. The final disposition of the patient will be noted (admission, discharge, or leaving against medical advice). The study will be approved by the institutional review board, and informed written consent will be obtained from all patients.

Statistical assessment will be using bivariate $X^2$ analysis and analysis of variance or covariance (ANCOVA), multivariate logistic regression. Covariates will be included in some multivariate models. Analyses will be performed by using the SAS software. Certain statistical values are expressed with 90% confidence intervals (CIs).

The above clinical trials may be split into two separate studies. One study will be an active controlled study comparing the injectable product described herein with diphenhydramine injection. The other will be a placebo controlled study comparing the invention injectable product with a placebo. The above 3-arm clinical trial may also be conducted as a single 2-arm study: a placebo controlled study comparing the invention injectable product against a placebo.

In addition, pediatric studies will be conducted on patients younger than the age of 12 with similar study design and lower drug dosage.

Prompt treatment with antihistamines is highly recommended to alleviate the symptoms of acute allergic reactions. Antihistamines are helpful in reducing histamine-mediated vasodilation and secondary edema. Commonly used drugs such as diphenhydramine injection provide $H_1$ blockade. Diphenhydramine reduces vasodilation in small blood vessels in the nose, eyes, and airways and provide some anticholinergic effects toward drying secretions. Diphenhydramine injection (1 to 2 mg/kg, up to a maximum of 50 mg, given IV or IM) is the drug of choice when treating acute allergic reactions. Concomitant administration of an $H_2$ agonist such as ranitidine (1 mg/kg IV) or cimetidine (4 mg/kg IV) is also of value to provide antihistaminic effect.

Currently, the only antihistamine injection existing on the market is diphenhydramine injection, a first generation antihistamine, with known side effects of cardio toxicity (QT prolongation), severe sedation, anti-cholinergic effect, potential of drug/drug interaction, and short acting which requires 3-4 doses a day. Cardio toxicity presents a huge safety concern, and the sedation side effect causes significantly inconvenience and discomfort for patients. The sedating side effect presents a safety concern when patients have to drive home themselves after being discharged from the emergency room. The sedating side effect also interferes with neurological exams for patients who are in need such exams in the hospital. Patients with allergic reactions to opioids are treated with diphenhydramine injections. This causes a dangerous additive effect in sedation. Diphenhydramine's QT prolongation is potentially life threatening and could lead to hospital admission. Sometimes acute allergic patients come to the ER and already took a few diphenhydramine tablets. ER doctors then put the patients on injection diphenhydramine as a standard procedure. This accumulated diphenhydramine concentration could cause cardiac arrest leading to hospital admission. QT prolongation is worsened by drug/drug interaction. In ICUs, diphenhydramine injection is frequently used as a preventive measure to desensitize antibiotics (antibiotics have a high incidence for drug induced allergic shock). In ICUs, patients are normally on multiple medications, and the potential drug/drug interaction and liver enzyme P450 inhibition leading to cardiac arrest due to QT prolongation is extremely dangerous. Diphenhydramine injection is commonly used together with blood transfusion to prevent acute allergic reactions to blood or plasma. Clearly sedation is unwanted. Diphenhydramine injection is often used to treat anesthesia induced acute allergies in the operating room. It takes longer for patients to awake from the anesthesia when diphenhydramine injection is co-used.

Therefore there is a great advantage and unmet medical need for a non-sedating antihistamine injection with longer duration of action, and without QT prolongation or anticholinergic effect, for the treatment of acute allergic reactions in humans and other mammals.

In one embodiment, the present disclosure includes injectable formulations of second and third generation antihistamines, or non-sedating antihistamines, for the treatment of acute allergic reactions (acute urticaria or angioedema associated with acute allergic reactions, optionally including anaphylaxis), via intravenous, intramuscular, or subcutaneous administration to provide an immediate onset of action. Such second and third generation antihistamines are commercially available as oral dosage forms as shown in the following table for the treatment of chronic allergies, such as seasonal/perennial rhinitis, and chronic idiopathic urticaria.

Additional non-sedating antihistamines as an injectable form for the treatment of acute allergic reactions, or symptoms (acute urticaria, angioedema, etc.) associated with acute allergic reactions optionally including anaphylaxis, include fexofenadine, loratadine, desloratadine, levocetirizine, desdiphenhydramine, epinastine, azelastine, Acrivastine, Ebastine, carbastine, levocarbastine, Mizolastine, and/or Rupatadine.

In accordance with some embodiments, an injectable solution comprising cetirizine or a pharmaceutically acceptable salt, isomer (e.g., levocetirizine), polymorph, thereof is provided. The injectable is suitable for intramuscular or intravenous injection. In some embodiments, the injection is particularly suitable for intravenous injection.

Parenteral injectable formulations may be in unit dose form in ampoules, small volume parenteral (SVP) vials, large volume parenterals (SVP), pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, buffering, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

Parenteral injectable formulations are typically aqueous solutions which may contain excipients such as salts, carbohydrates and buffering agents (preferably at a pH of from 3 to 9.5), but, for some applications, they may be more suitably formulated as a sterile non-aqueous solution or as a dried form to be used in conjunction with a suitable vehicle such as sterile, pyrogen-free water.

In one embodiment, the injectable compositions contain a solution of cetirizine or a pharmaceutically acceptable salt, isomer, polymorph, thereof in an aqueous solvent combined with pH adjusting agents having a pH of about 5.5+/−1.0 and least one isotonicity agent. A water-insoluble inert gas may be carefully bubbled through the solvent to remove oxygen from the medium. Optionally the compositions contain at least one preservative and/or at least one solubility enhancing agent and/or at least one stabilizing agent, and/or at least one absorption enhancer. In some embodiments, the composition is substantially free of stabilizing agents and preservatives.

In one embodiment, the quantity of cetirizine or salt, isomer, polymorph, thereof in the injection formulation is 2-20 mg per milliliter of liquid, preferably 3-15 mg, more preferably about 3.5-10 mg per milliliter of liquid.

In another embodiment, the non-sedating H1 antihistamines is fexofenadine or a salt thereof. In yet another embodiment, the quantity of fexofenadine or salt thereof in the injection formulation is 1-200 mg per milliliter of liquid, preferably 1.5-180 mg, preferably 2-90 mg, more preferably 2.5-70 mg per milliliter of liquid.

In another embodiment, the injectable composition optionally comprises at least one H2 antihistamine, specifically ranitidine and cimetidine, more specifically ranitidine. Concomitant administration of an H2 agonist such as ranitidine (1 mg/kg IV) or cimetidine (4 mg/kg IV) may be of value to provide antihistaminic effect.

In some embodiments, the injectable comprises a single dose pH adjusted (about pH 5.5+/−1.0) solution having an effective amount of cetirizine or a pharmaceutically acceptable salt, isomer, polymorph, thereof for treating symptoms of acute allergic reaction; a tonicity agent for adjusting osmolality to about physiological osmolality; optional pH adjusting reagents; and sterile water for injection.

The single dose may be from about 0.2 mL to about 10 mL in total injection volume, and may take the form of a small volume parenteral (SVP) injection. In some embodiments, the total injection volume is about 0.5 mL to about 5 mL. In still others, the total injection volume is about 2 mL. In other embodiments, the total injection volume is about 1 mL. A 1 mL dose is well suited to an injection because it is easily introduced. Single dosage SVP vials provide ease of storage, measurement and dosing, particularly in a hectic emergency situation.

Cetirizine or a pharmaceutically acceptable salt, isomer, polymorph, thereof, will be present in an amount effective to treat acute allergic reaction symptoms, about 2 mg to about 20 mg per dose. Adult dosages will be approximately 10 mg per dose. Given the volume sizes, cetirizine or a pharmaceutically acceptable salt, isomer, polymorph, thereof will be present at about 0.1% to about 2% w/v. In some embodiments, cetirizine or a pharmaceutically acceptable salt, isomer, polymorph, thereof will be present at about 0.2% to about 1.5% w/v. In some embodiments, cetirizine or a pharmaceutically acceptable salt, isomer, polymorph thereof will be present at about 0.25% to about 1% w/v. In some embodiments, cetirizine or a pharmaceutically acceptable salt, isomer, polymorph thereof will be present at about 0.5% to about 1% w/v. In a 1 mL dose, a suitable dose is about 1% w/v of cetirizine or a pharmaceutically acceptable salt, isomer, polymorph, thereof.

Tonicity agents are sometimes present. The term "tonicity agent" refers to a pharmaceutically acceptable excipient that makes the solution compatible with blood. Suitable tonicity agents include glycerin, lactose, mannitol, dextrose, sodium chloride, sodium sulfate, sorbitol and the like. Preferred tonicity agents include mannitol, sorbitol, lactose and sodium chloride and combinations thereof, and most particularly, sodium chloride. The tonicity agent is added to the injectable to achieve substantially physiological osmolality for injection.

Physiological osmolality, as used herein, is about 255 mOsm/kg to about 315 mOsm/kg. An injectable having an osmolality in this range is said to be isotonic. Hypertonic and hypotonic solutions both present complications and undesirable effects when injected. The injectables described herein are isotonic to minimize or avoid such effects. Since osmolality is the measure of particles in a solution, every component added to the injectable affects the osmolality, thus, adjusting to a final osmolality is complicated, particularly when also adjusting the pH, as addition of the tonicity agent may affect pH and addition of the pH adjusting reagents will affect tonicity.

Optional pH adjusting reagents include acids and bases, such as but not limited to dilute HCl and NaOH. An acid may be added to lower the pH, while the base is added to raise pH. In some instances one or both an acid and a base may be used. In some embodiments, the pH adjusting reagents are chosen to complement the tonicity agent to provide similar ions when in solution. For example, when NaCl is used as a tonicity agent, HCl and/or NaOH may be used as the pH adjusting reagents.

Sterile water for injection is used to increase the volume of the injectable to the desired level.

Injectables in accordance with some embodiments comprise:
a total injection volume of about 0.2 mL to about 10 mL;
an effective amount of cetirizine or a pharmaceutically acceptable salt, polymorph, thereof, or about 2 mg to about 20 mg;
a tonicity agent in an amount to achieve physiological osmolality;
a pH adjusting reagent such as an acid and/or a base to adjust pH to about 5.5+/−1.0;
q.s. sterile water for injection.

In some embodiments, the total injection volume is about 0.5 mL to about 5 mL. For ease of measurement, storage and dosage measurement, the injectable is provided in a single dosage form. In some instances, the total injection volume is 1 mL. The total injection volume contains an effective amount of cetirizine. Smaller volumes therefore will have a higher concentration of cetirizine. For example, a dose of about 10 mg of cetirizine in a 1 mL total volume injectable is about 1% w/v with respect to cetirizine, salt, isomer or polymorph.

In some embodiments, an isomer of cetirizine injection, such as levocetirizine injection, may be used. Particularly, levocetirizine may be used in about half of the amounts of cetirizine.

The tonicity agent, such as NaCl, is employed to achieve an isotonic solution. Isotonic solutions for injection have an osmolality roughly equivalent to physiological osmalality, which as used herein is about 255 mOsm/kg to about 315 mOsm/kg. In the exemplary 1% w/v cetirizine HCl 1 mL injectable, it has been found that about 0.65% NaCl yields an osmolality within the physiological range (when the solution is pH adjusted to pH about 5.5+/−1.0). Other concentrations of NaCl resulted in either undesirable hypertonic or hypotonic solutions.

In some embodiments, the injectable formulation is substantially free of buffers, contrary to most injectable formulations. Surprisingly, this unique buffer free formulation described herein maintained its pH values upon heat storage at 60° C. and maintained its stability. The benefit of this buffer free formulation allows immediate and ease dilution by the blood flow upon injection to the patient's blood circulation. In some embodiments, the formulation is substantially free of preservatives. As discussed below, an exemplary formulation was stable during an accelerated stability test for up to 5 days at 60° C. Thus, the injectable is stable and has a long shelf life.

Additional components, such as active agents, excipients, diluents, buffers, preservatives, etc. may be employed, so long as the injectable remains isotonic and stable. Any suitable additional active agent could optionally be incorporated into the injectable, provided that the additional active agent is not an NSAID.

As noted above, H2 antagonists, such as ranitidine or cimetidine are suitable additional active agents. Other possibilities include, but are not limited to famotidine and nizatidine.

One exemplary injectable in accordance with some embodiments comprises:
a 1 mL total injection volume;
about 10 mg cetirizine or a pharmaceutically acceptable salt, polymorph, thereof;
about 6.5 mg NaCl;
HCl and/or NaOH to pH 5.5+/−1.0; and
q.s. sterile water for injection.

In some embodiments, the injectable formulation is substantially free of buffers. In some embodiments, the formulation is substantially free of preservatives.

In some embodiments, an isomer of cetirizine may be used. Particularly, levocetirizine may be used in about half of the amounts of cetirizine.

Injectables in accordance with some embodiments consist essentially of:
a total injection volume of about 0.5 mL to about 5 mL;
an effective amount of cetirizine, or a pharmaceutically acceptable salt, polymorph, thereof, or about 1 mg to about 20 mg cetirizine;
a tonicity agent in an amount to achieve physiological osmolality;
a pH adjusting reagent such as an acid and/or a base to adjust pH to about 3-9, preferably about 5.5+/−1.0; and q.s. sterile water for injection.

In some embodiments, an isomer of cetirizine may be used. Particularly, levocetirizine may be used in about half of the amounts.

One exemplary injectable in accordance with some embodiments of the invention consists essentially of:
a 1 mL total injection volume;
about 10 mg cetirizine, or a pharmaceutically acceptable salt, polymorph, thereof;
about 6.5 mg NaCl;
HCl and/or NaOH to pH about 5.5+/−1.0; and
q.s. sterile water for injection.

In some embodiments, an isomer of cetirizine may be used. Particularly, levocetirizine may be used in half of the amounts used in cetirizine formulations.

In some embodiments, the injectable formulation is substantially free any additional components.

One embodiment provides an injectable formulation comprising:

| Component | % w/v | Mg/mL |
| --- | --- | --- |
| Cetirizine HCl, USP or EP | 1.00 | 10.00 |
| Sodium chloride, USP | 0.65 | 6.5 |
| Sodium hydroxide (pellets), NF | q.s. to adjust pH to about 5.5 +/− 1.0 | q.s. to adjust pH to about 5.5 +/− 1.0 |
| Diluted HCl, NF | q.s. to adjust pH to about 5.5 +/− 1.0 | q.s. to adjust pH to about 5.5 +/− 1.0 |
| Water for injection, USP | q.s. to 100% | q.s. to 1.00 mL |

Another embodiment provides an injectable formulation comprising:

| Component | % w/v | Mg/mL |
| --- | --- | --- |
| Cetirizine HCl, USP or EP | 1.00 | 10.00 |
| Sodium chloride, USP | 0.65 | 6.5 |
| Benzyl Alcohol | 0.9% | 9.0 |

-continued

| Component | % w/v | Mg/mL |
|---|---|---|
| Sodium hydroxide (pellets), NF | q.s. to adjust pH to about 5.5 +/− 1.0 | q.s. to adjust pH to about 5.5 +/− 1.0 |
| Diluted HCl, NF | q.s. to adjust pH to about 5.5 +/− 1.0 | q.s. to adjust pH to about 5.5 +/− 1.0 |
| Water for injection, USP | q.s. to 100% | q.s. to 1.00 mL |

In an embodiment, an injectable composition, on per milliliter level, comprises 2 to 20 mg of cetirizine, 1 to 9 mg of sodium chloride, and 2 to 20 mg of benzyl alcohol, specifically 2 to 9 mg benzyl alcohol, and water q.s. to 100%, adjusted to a pH of about 5.5+/−1.0. In another embodiment, an injectable composition, particularly for intramuscular injection consists essentially of 2 to 20 mg of cetirizine, 1 to 9 mg of sodium chloride, and 2 to 20 mg of benzyl alcohol, specifically 2 to 9 mg benzyl alcohol, and water q.s. to 100%, adjusted to a pH of about 5.5+/−1.0. In yet another embodiment, an injectable composition, particularly for intramuscular injection consists of 2 to 20 mg of cetirizine, 1 to 9 mg of sodium chloride, and 2 to 20 mg of benzyl alcohol, specifically 2 to 9 mg benzyl alcohol, and water q.s. to 100%, adjusted to a pH of about 5.5+/−1.0.

Due to the fast onset of acute allergic reactions including anaphylaxis, often patients do not have sufficient time to reach medical care facilities for treatment. In this life and death situation, it is important that patients administer medications to themselves immediately. Accordingly, there is a need in the art to develop injectable formulations and optionally self operated and ready to use auto injector products, needle or needleless, providing a rapid delivery of the injectable non-sedating antihistamine formulation.

An automatic injector or auto-injector is a device designed to allow a user to self-administer a pre-measured dose of a medicament composition subcutaneously or intramuscularly, usually in an emergency situation. A typical auto-injector has a housing, inside of which is a cartridge. The cartridge has one or several chambers containing medicament compositions or components thereof and is in communication with a dispensing assembly such as needle assembly. The cartridge can hold either a pre-mixed liquid medicament or a solid medicament and a liquid that are mixed prior to injection. The housing carries an actuation assembly with a stored energy source, for example, a compressed spring. Activation of the actuation assembly causes a sequence of movements, whereby the needle extends from the auto-injector into the user so that the medicament compound is then forced through the needle and into the user. After delivery of the dose of medicament into the injection site, the needle remains in an extended position or in a hidden position. If the auto-injector is of the type designed to carry plural components of the medicament composition in separate, sealed compartments, structure may be included that forces the components to mix when the actuation assembly is activated.

Auto-injectors for antihistamine administration are not currently marketed and have never existed. Advantages of the use of auto-injectors to dispense non-sedating (second and third generation) antihistamines for the treatment of severe and acute allergic reactions include availability for emergency treatment, precise dosing, portability, readiness for use, rapid intramuscular or subcutaneous administration, administration through clothing and protective wear, and rapid self-administration. The advantages of this invention also include its non-cardiotoxicity (no QT prolongation), and non-sedating. Unlike the current highly sedating diphenhydramine injections, the non-sedating feature of this invention allows patients to be alert enough to drive to the hospital or emergency care facility after they self administer the non-sedating antihistamine injection via an auto-injector.

In another embodiment, a kit comprises the automatic injector comprising a non-sedating antihistamine injectable composition as described above, and a second automatic injector comprising a second housing comprising a second chamber for an epinephrine composition and a second dispensing assembly in communication with the second chamber.

In one embodiment, disclosed herein is an injectable second or third generation antihistamine (non-sedating antihistamine) formulation. Also disclosed are methods of treating an acute allergic reaction or symptoms (acute urticaria, angioedema, etc.) associated with acute allergic reactions optionally including anaphylaxis, comprising administering to an individual in need thereof an effective amount of an injectable composition comprising a second or third generation antihistamine (or non-sedating antihistamine), wherein the individual is a human or other mammal. In specific embodiments, the antihistamine is not diphenhydramine. In other embodiments, the non-sedating antihistamine is selected from cetirizine, loratadine, levocetirizine, desloratadine, and fexofenadine, des-diphenhydramine, epinastine, azelastine, Acrivastine, Ebastine, carbastine, levocarbastine, Mizolastine, and Rupatadine.

In one embodiment, the injectable formulation further comprises at least one H2 receptor antagonist, such as ranitidine or cimetidine. In another embodiment, the injectable formulation further comprises epinephrine. In yet another embodiment, the injectable formulation further comprises at least one steroid, such as methylprednisolone or prednisolone.

In one embodiment, disclosed herein are methods of treating an acute allergic reaction or its symptoms comprising administering to an individual in need thereof an effective amount of an injectable composition comprising a second or third generation antihistamine (or non-sedating antihistamine), wherein the injectable composition is bioequivalent on AUC to an oral formulation of the $2^{nd}$ or $3^{rd}$ generation antihistamine.

| Non-sedating Antihistamine | Oral product | Dosage range of injectable formulation |
|---|---|---|
| Cetirizine | 10 mg tablet<br>10 mg chewable tablet<br>10 mg capsule<br>5 mg tablet<br>5 mg/5 mL syrup | about 2 mg to about 20 mg |
| Loratadine | 10 mg tablet<br>10 mg capsule<br>5 mg tablet<br>5 mg chewable tablet<br>0.5 mg/mL syrup<br>1 mg/mL suspension<br>1 mg/mL syrup | about 1 mg to about 20 mg |
| Fexofenadine | 180 mg tablet/capsule<br>60 mg tablet<br>30 mg tablet<br>30 mg/5 mL suspension | about 5 mg to about 180 mg |
| Levocetirizine | 5 mg tablet<br>2.5 mg tablet<br>2.5 mg/5 mL syrup | about 1 mg to about 10 mg |
| Desloratadine | 5 mg tablet<br>2.5 mg/5 mL syrup | about 1 mg to about 10 mg |

As used herein, the term equivalent to an oral product means that the 90% confidence limits of a ratio of a logarithmic transformed geometric mean of $AUC_{0-INF}$ and/or $AUC_{0-t}$ for the injectable formulation to a logarithmic transformed geometric mean of $AUC_{0-INF}$ and/or $AUC_{0-t}$ for the reference oral product are about 0.80 to about 1.25, specifically 0.80 to 1.25. "AUC" is the area under the curve of a graph of the measured concentration of an active agent (typically plasma concentration) vs. time, measured from one time point to another time point. For example $AUC_{0-t}$ is the area under the curve of plasma concentration versus time from time 0 to time t, the last blood draw time point. The $AUC_{0-\infty}$ or $AUC_{0-INF}$ is the calculated area under the curve of plasma concentration versus time from time 0 to time infinity by extrapolation. In one embodiment, the $AUC_{0-INF}$ and/or $AUC_{0-t}$ are given in Table 2. In another embodiment, the $AUC_{INF}$ and/or $AUC_{0-t}$ for the injectable formulation and the reference oral dosage form are determined in a reference-controlled study.

In one embodiment, disclosed herein are methods of treating an acute allergic reaction or its symptoms: acute urticaria, angioedema, etc., associated with acute allergic reactions optionally including anaphylaxis comprising administering to an individual in need thereof an effective amount of an injectable composition comprising a second or third generation antihistamine (or non-sedating antihistamine), wherein the injectable composition is therapeutically equivalent to a reference diphenhydramine injectable formulation. In one embodiment, the reference diphenhydramine injectable formulation is a 50 mg/mL solution, and the dose is about 12.5-150 mg dose. Diphenhydramine injection is commercially available from Pfizer as Benadryl® Injection. Many generic versions of diphenhydramine injections are also available on the market. Therapeutic equivalence can be determined in a reference-controlled study using a diphenhydramine injectable formulation as the reference.

As used herein, therapeutically equivalent to a reference diphenhydramine injectable formulation means that the test formulation has a 90% confidence interval around the difference in the reduction of at least one symptom of an acute allergic reaction including anaphylaxis of the test drug to the reference drug, for the per protocol evaluable population, within about −30.00 to about +30.00. In specific embodiments, the symptoms of anaphylaxis or an acute allergic reaction are, pruritus severity, pruritus duration, erythema, angioedema and/or wheezing reduction, and acute urticaria severity, number/areas of urticaria, or erythema areas.

Predicted results for clinical equivalence are presented in Table 3:

| Treatment | N | Baseline | On Treatment adjusted mean | Difference from Placebo | 90% CI (−30.00, +30.00) |
|---|---|---|---|---|---|
| Pruritus severity score reduction ||||||
| Cetirizine 10 mg injection | About 100 | About 2.80 | About 1.70 | +0.05 | About (−3.00, 8.00) |
| Diphenhydramine 50 mg injection | About 100 | About 2.75 | About 1.65 | | |
| Erythema Reduction ||||||
| Cetirizine 10 mg injection | About 100 | About 2.50 | About 1.0 | 0.00 | About (−10.00, 10.00) |
| Diphenhydramine 50 mg injection | About 100 | About 2.55 | About 1.0 | | |
| Angioedema Reduction ||||||
| Cetirizine 10 mg injection | About 100 | About 2.50 | About 1.0 | −0.25 | About (−10.00, 8.00) |
| Diphenhydramine 50 mg injection | About 100 | About 2.45 | About 1.25 | | |
| Number of urticaria areas ||||||
| Cetirizine 10 mg injection | About 100 | About 4.2 | About 1.0 | −0.20 | About (−10.00, 8.00) |
| Diphenhydramine 50 mg injection | About 100 | About 4.0 | About 1.20 | | |

Expected results for effectiveness comparing to placebo are presented in Table 4:

| Treatment | N | Baseline | On Treatment adjusted mean | Difference from Placebo | P-value |
|---|---|---|---|---|---|
| Pruritus severity score reduction ||||||
| Cetirizine 10 mg injection | About 100 | About 2.80 | About 1.80 | −0.70 | <0.05 |
| Placebo injection | About 100 | About 2.75 | About 2.50 | | |
| Erythema Reduction ||||||
| Cetirizine 10 mg injection | About 100 | About 2.50 | About 1.0 | −1.15 | <0.05 |
| Placebo injection | About 100 | About 2.55 | About 2.15 | | |

-continued

| Treatment | N | Baseline | On Treatment adjusted mean | Difference from Placebo | P-value |
|---|---|---|---|---|---|
| Angioedema Reduction ||||||
| Cetirizine 10 mg injection | About 100 | About 2.50 | About 1.0 | −1.25 | <0.05 |
| Placebo injection | About 100 | About 2.45 | About 2.25 | | |
| Number of urticaria areas ||||||
| Cetirizine 10 mg injection | About 100 | About 4.2 | About 1.0 | −2.8 | <0.05 |
| Placebo injection | About 100 | About 4.0 | About 3.8 | | |

In one embodiment, disclosed herein are methods of treating an acute allergic reaction or its symptoms: acute urticaria, angioedema, etc, associated with acute allergic reaction optionally including anaphylaxis comprising administering to an individual in need thereof an effective amount of an injectable composition comprising a second or third generation antihistamine, the non-sedating antihistamine, wherein the injectable composition is therapeutically effective compared to placebo. As used herein, a placebo is an inactive pill, liquid, or powder that has no treatment value. In clinical trials, experimental treatments are often compared with placebos to assess the treatment's effectiveness. A placebo-controlled study is a method of investigation of drugs in which an inactive substance (the placebo) is given to one group of participants, while the drug being tested is given to another group. The results obtained in the two groups are then compared to see if the investigational treatment is more effective in treating the condition than the placebo.

As used herein, therapeutically effective compared to placebo means that the treatment of this invention is statistically superior ($p<0.05$) to a placebo in the reduction of at least one symptom of anaphylaxis or an acute allergic reaction, wherein the symptom is pruritus severity, pruritus duration, erythema, angioedema, acute urticaria, number of urticaria, urticaria areas, erythema areas, and/or wheezing.

The methods described herein optionally further comprise administering a second active agent as well as the second or third generation antihistamine. In one embodiment, the second active agent is an H2 receptor antagonist, such as ranitidine or cimetidine. In another embodiment, the second active agent is epinephrine. In yet another embodiment, the second active agent comprises at least one steroid, such as methylprednisolone or prednisolone. In one embodiment, the methods disclosed herein further comprise administering a second active agent comprising ranitidine, cimetidine, epinephrine, methylprednisolone, prednisolone, or a combination thereof.

The invention is further illustrated by the following examples:

Example 1

Phase I Clinical Study of IV and IM Cetirizine Injection

The study was a phase I clinical study to investigate the pharmacokinetics (PK) together with the safety and tolerability of cetirizine injection at 5 mg and 10 mg intravenous doses and a 10 mg intramuscular dose, in comparison to the marketed cetirizine oral product Zyrtec® 10 mg tablets (an OTC product) in 24 healthy male and female volunteers after a single dose administration. The study was a single center, randomized, single dose, laboratory-blinded, 4-period, 4-sequence, crossover design. Twenty-four subjects were included.

In each study period, one of the following treatments was administered in the morning after a 10-hour overnight fast, as follows:

| | | |
|---|---|---|
| Treatment-A: | Zyrtec ® 10 mg tablet (Reference) | |
| | Dose: | A single 10 mg dose of cetirizine |
| | Dosage form: | One tablet |
| | Administration: | By the oral route with about 240 mL of water |
| Treatment-B: | Cetirizine 10 mg/mL injection (Test) | |
| | Dose: | A single 10 mg dose of cetirizine |
| | Injection volume: | 1.0 mL |
| | Administration: | Intramuscular injection, using an 1" needle, in the anterolateral thigh muscle slowly within a period of 0.5 minute |
| Treatment-C: | Cetirizine 10 mg/mL injection (Test) | |
| | Dose: | A single 5 mg dose of cetirizine |
| | Injection volume: | 0.5 mL |
| | Administration: | Intravenous injection over a period of 1 to 1.5 minute via an indwelling catheter |
| Treatment-D: | Cetirizine 10 mg/mL injection (Test) | |
| | Dose: | A single 10 mg dose of cetirizine |
| | Injection volume: | 1.0 mL |
| | Administration: | Intravenous injection over a period of 1 to 1.5 minute via an indwelling catheter |

Subjects remained in bed for at least the first 1 hour following drug administration.

In each study period, twenty-two (22) blood samples (1×4 mL each) were collected by catheter in pre-cooled Vacutainers containing EDTA, as follows:

The first blood sample was collected prior to drug administration

During the first hour post drug administration, blood samples were collected 2, 4, 6, 8, 10, 15, 20, 30, 45 and 60 minutes post drug administration. In the study periods where the drug is administered by intravenous injection, these blood samples were obtained from the arm opposite to that used for the injection.

Subsequently, blood samples were collected 1.33, 1.67, 2, 2.5, 3, 4, 6, 10, 18, 24 and 36 hours post drug administration.

A questionnaire was completed prior to and approximately 1, 4 and 12 hours after drug administration to evaluate mental sedation, physical sedation and dry mouth.

Cetirizine plasma concentrations were measured by a validated analytical method.

Main absorption and disposition parameters using a non-compartmental approach with a log-linear terminal phase assumption were used. A trapezoidal rule to estimate the area under the curve was used. The pharmacokinetic parameters of interest for this study were the ln-transformed $AUC_\infty$. Other parameters including $C_{max}$, $AUC_T$, $AUC_\infty$, $T_{max}$, $AUC_{T/\infty}$, $K_{el}$, $T_{1/2el}$, F, $Cl_{TOT}$ and $V_D$ were calculated.

Statistical analysis of all pharmacokinetic parameters was based on a parametric ANOVA model.

The 90% confidence interval for the exponential of the difference in LSmeans between Treatment-A and Treatment-D, Treatment-A and Treatment-B, Treatment-C and Treatment-D, and Treatment-B and Treatment-D was calculated for the ln-transformed parameter AUG, for all comparisons. For Dose proportionality assessment between Treatment-C and Treatment-D, dose normalized arithmetic and geometric mean ratios and their two-sided 90% confidence intervals was calculated from the ln-transformed pharmacokinetic parameter $AUC_\infty$.

Pharmacokinetic endpoints were as follows:
For Treatment-A versus Treatment-D:
Statistical inference of cetirizine based on a bioequivalence approach using the following standards:
If the ratio of geometric LSmeans with corresponding 90% confidence interval calculated from the exponential of the difference between Treatment-A and Treatment-D for the ln-transformed parameter $AUC_\infty$ is within the 80 to 125% range, the two treatments are deemed bioequivalent on drug exposure
If the ratio of geometric LSmeans with corresponding 90% confidence interval calculated from the exponential of the difference between Treatment-A and Treatment-D for the ln-transformed parameters $AUC_\infty$ and $C_{max}$ is within the 80 to 125% range, the two treatments are deemed bioequivalent.

For Treatment-A versus Treatment-B:
Statistical inference of cetirizine based on a bioequivalence approach using the following standards:
If the ratio of geometric LSmeans with corresponding 90% confidence interval calculated from the exponential of the difference between Treatment-A and Treatment-B for the ln-transformed parameter $AUC_\infty$ is within the 80 to 125% range, the two treatments are deemed bioequivalent on drug exposure
If the ratio of geometric LSmeans with corresponding 90% confidence interval calculated from the exponential of the difference between Treatment-A and Treatment-B for the ln-transformed parameters $AUC_\infty$ and $C_{max}$ is within the 80 to 125% range, the two treatments are deemed bioequivalent.

Dose Proportionality between Treatment-C and Treatment-D:
The 5 mg and 10 mg single doses of Cetirizine intravenous injections will be assessed for proportionality based on the following:
If the ratio of dose normalized geometric LSmeans with corresponding 90% confidence interval calculated from the exponential of the difference between Treatment-C and Treatment-D for the ln-transformed parameters $C_{max}$ is within the 80 to 125% range, the two treatments are deemed dose proportional on $C_{max}$.
If the ratio of dose normalized geometric LSmeans with corresponding 90% confidence interval calculated from the exponential of the difference between Treatment-C and Treatment-D for the ln-transformed parameters $AUC_\infty$ is within the 80 to 125% range, the two treatments are deemed dose proportional on drug exposure.

For Treatment-B versus Treatment-D:
Statistical inference of cetirizine based on a bioequivalence approach using the following standards:
If the ratio of geometric LSmeans with corresponding 90% confidence interval calculated from the exponential of the difference between Treatment-B and Treatment-D for the ln-transformed parameter $AUC_\infty$ is within the 80 to 125% range, the two treatments are deemed bioequivalent on drug exposure.
If the ratio of geometric LSmeans with corresponding 90% confidence interval calculated from the exponential of the difference between Treatment-B and Treatment-D for the ln-transformed parameters $AUC_\infty$ and $C_{max}$ is within the 80 to 125% range, the two treatments are deemed bioequivalent.

The injectable cetirizine product was provided as a sterile, isotonic, aqueous solution without preservatives. It is a small volume parenteral (SVP) of 1 mL fill size in a 2-mL vial. The excipients in the product are sodium chloride as the tonicity agent and NaOH/HCl as the pH adjusters to pH 5.2 (4.5 to 6).

In the following tables:

| Treatment-A: | Zyrtec ® 10 mg tablet (Reference) | |
|---|---|---|
| | Dose: | A single 10 mg dose of cetirizine |
| | Dosage form: | One tablet |
| | Administration: | By the oral route with about 240 mL of water |
| Treatment-B: | Cetirizine 10 mg/mL injection (Test) | |
| | Dose: | A single 10 mg dose of cetirizine |
| | Injection volume: | 1.0 mL |
| | Administration: | Intramuscular injection in the anterolateral thigh muscle slowly within a period of 0.5 minute |
| Treatment-C: | Cetirizine 10 mg/mL injection (Test) | |
| | Dose: | A single 5 mg dose of cetirizine |
| | Injection volume: | 0.5 mL |
| | Administration: | Intravenous injection over a period of 1 to 1.5 minute via an indwelling catheter |
| Treatment-D: | Cetirizine 10 mg/mL injection (Test) | |
| | Dose: | A single 10 mg dose of cetirizine |
| | Injection volume: | 1.0 mL |
| | Administration: | Intravenous injection over a period of 1 to 1.5 minute via an indwelling catheter |

In Data Table 1, a 10 mg Zyrtec® tablet is compared to a 10 mg cetirizine IV injection.

Data Table 1

| PARAMETER | Treatment A (Tablet 10 mg) | | Treatment D (IV injection 10 mg) | |
|---|---|---|---|---|
| | Mean | C.V. | Mean | C.V. |
| Cmax (ng/mL) | 318.04 | 18.7 | 1343.53 | 71.9 |
| ln(Cmax) | 5.7450 | 3.3 | 7.0580 | 7.0 |
| $T_{max}$ (hours) | 0.75 | 55.9 | 0.03 | 327.5 |
| $AUC_T$ (ng · h/mL) | 2547.19 | 15.8 | 2639.54 | 20.3 |
| ln($AUC_T$) | 7.8304 | 2.1 | 7.8595 | 2.5 |
| $AUC_\infty$ (ng · h/mL) | 2650.73 | 15.9 | 2745.30 | 20.1 |
| ln($AUC_\infty$) | 7.8698 | 2.1 | 7.8984 | 2.5 |

The ratio of geometric LSmeans with corresponding 90% confidence interval calculated from the exponential of the difference between Treatment A and Treatment D for the ln-transformed parameter $AUC_\infty$ is within the 80 to 125% range, therefore, the two treatments are deemed bioequivalent on drug exposure.

In Data Table 2, a 10 mg Zyrtec® tablet is compare to a 10 mg cetirizine intramuscular injection.

| | Data Table 2 | | | |
|---|---|---|---|---|
| | Treatment A (Tablet 10 mg) | | Treatment B (IM injection 10 mg) | |
| PARAMETER | Mean | C.V. | Mean | C.V. |
| Cmax (ng/mL) | 318.04 | 18.7 | 173.55 | 17.7 |
| ln(Cmax) | 5.7450 | 3.3 | 5.1420 | 3.4 |
| $T_{max}$ (hours) | 0.75 | 55.9 | 4.00 | 20.3 |
| $AUC_T$ (ng·h/mL) | 2547.19 | 15.8 | 2619.60 | 13.7 |
| $ln(AUC_T)$ | 7.8304 | 2.1 | 7.8616 | 1.8 |
| $AUC_\infty$ (ng·h/mL) | 2650.73 | 15.9 | 2771.70 | 15.1 |
| $ln(AUC_\infty)$ | 7.8698 | 2.1 | 7.9159 | 2.0 |

The ratio of geometric LSmeans with corresponding 90% confidence interval calculated from the exponential of the difference between Treatment A and Treatment B for the ln-transformed parameter $AUC_\infty$ is within the 80 to 125% range, therefore, the two treatments are deemed bioequivalent on drug exposure.

In Data Table 3, a 10 mg cetirizine intramuscular injection is compared to a 10 mg cetirizine intravenous injection.

| | Data Table 3 | | | |
|---|---|---|---|---|
| | Treatment B (IM injection 10 mg) | | Treatment D (IV injection 10 mg) | |
| PARAMETER | Mean | C.V. | Mean | C.V. |
| Cmax (ng/mL) | 173.55 | 17.7 | 1343.53 | 71.9 |
| ln(Cmax) | 5.1420 | 3.4 | 7.0580 | 7.0 |
| $T_{max}$ (hours) | 4.00 | 20.3 | 0.03 | 327.5 |
| $AUC_T$ (ng·h/mL) | 2619.60 | 13.7 | 2639.54 | 20.3 |
| $ln(AUC_T)$ | 7.8616 | 1.8 | 7.8595 | 2.5 |
| $AUC_\infty$ (ng·h/mL) | 2771.70 | 15.1 | 2745.30 | 20.1 |
| $ln(AUC_\infty)$ | 7.9159 | 2.0 | 7.8984 | 2.5 |

The ratio of geometric LSmeans with corresponding 90% confidence interval calculated from the exponential of the difference between Treatment B and Treatment D for the ln-transformed parameter $AUC_\infty$ is within the 80 to 125% range, therefore, the two treatments are deemed bioequivalent on drug exposure.

In Data Table 4, the dose proportionality of a 5 mg cetirizine IV injection is compared to a 10 mg cetirizine IV injection.

| | Data Table 4 | | | |
|---|---|---|---|---|
| | TREATMENT-C (IV injection 5 mg) | | TREATMENT-D (IV injection 10 mg) | |
| PARAMETER | MEAN | C.V. | MEAN | C.V. |
| $C_{max}$ (ng/mL) | 494.49 | 27.3 | 1343.53 | 71.9 |
| $ln(Cm_{ax})$ | 6.1692 | 4.3 | 7.0580 | 7.0 |
| $T_{max}$ (hours) | 0.05 | 34.1 | 0.03 | 327.5 |
| $AUC_T$ (ng·h/mL) | 1263.71 | 19.0 | 2639.54 | 20.3 |
| $ln(AUC_T)$ | 7.1232 | 2.8 | 7.8595 | 2.5 |
| $AUC_\infty$ (ng·h/mL) | 1318.85 | 18.7 | 2745.30 | 20.1 |
| $ln(AUC_\infty)$ | 7.1664 | 2.8 | 7.8984 | 2.5 |

The ratio of dose normalized geometric LSmeans with corresponding 90% confidence interval calculated from the exponential of the difference between Treatment C and Treatment D for the ln-transformed parameter $AUC_\infty$ is within the 80 to 125% range, therefore, the two treatments are deemed dose proportional on drug exposure AUC. However, the ratio of dose normalized geometric LSmeans with corresponding 90% confidence interval calculated from the exponential of the difference between Treatment C and Treatment D for the ln-transformed parameter Cmax is NOT within the 80 to 125% range, therefore, the two treatments are deemed not dose-proportional on Cmax.

In practice, the non-dose proportionality of administration of the injectable cetirizine dosage forms would lead a physician to adjust doses in a non-dose proportional manner. For example, if a normal dose is 10 mg, a physician may give smaller doses for less severe patients. If the physician wanted to use 50% of the dose, that would be 5 mg. But we know now that 5 mg does not generate 50% of the PK of the 10 mg, rather only ~37% of the PK from the 10 mg. This way the physician should in practice use a 6.8 mg dose, rather than 5 mg. Also if a patient is very severe and heavy in body weight, for example, the physician might want to double the dose to 20 mg. Due to the non dose-proportionality, the correct dose should be 15 mg rather than 20 mg.

The average alertness score was determined for all treatments to determine drowsiness in the subjects (N=24). A score of 1 is most drowsy, and a score of 10 is most alert. The average alertness score surprisingly showed the similar alertness levels for all 4 treatments as shown in Data Table 5.

| Data Table 5 | | | | | | | | | | | | | | | |
|---|---|---|---|---|---|---|---|---|---|---|---|---|---|---|---|
| Treatment A 10 mg oral | | | | Treatment B 10 mg IM | | | | Treatment C 5 mg IV | | | | Treatment D 10 mg IV | | | |
| pre | 1 hr | 4 hr | 12 hr | pre | 1 hr | 4 hr | 12 hr | pre | 1 hr | 4 hr | 12 hr | pre | 1 hr | 4 hr | 12 hr |
| 9.92 | 9.75 | 9.42 | 9.75 | 9.71 | 9.45 | 9.58 | 9.61 | 9.50 | 9.30 | 9.30 | 9.74 | 9.75 | 9.54 | 9.58 | 9.83 |

The following surprising conclusions can be drawn from this study:
1) It was reported by the Zyrtec® Product Insert that the cetirizine oral tablet has a bioavailability of about 70%, leading to the prediction that the AUC of the IV injection would be about 30% higher than the AUC of the oral tablet with the same mg of cetirizine. From our study, it was unexpectedly discovered that the AUC of the IV is equivalent to the AUC of the tablet with the same mg of cetirizine.
2) Surprisingly Cmax is not dose proportional between 10 mg and 5 mg IV, but AUC is dose proportional. This discovery is contrary to the pharmacokinetic information reported in the product insert of Zyrtec® oral tablet, further demonstrating the significant difference between cetirizine injection and cetirizine oral product. This discovery will enable proper dose adjustment when administering different dosages of cetirizine injection.
3) Drowsiness surprisingly was not increased for IV or IM injection compared to oral despite the high Cmax and quick drug appearance in blood stream, particularly for IV.
4) Surprisingly, the Cmax for IV injection is about 7.7 times of the Cmax for IM injection, but with about the same AUC.
5) Surprisingly, the Cmax for IV injection is about 4.2 times the Cmax for oral administration (it was previously projected, using pharmacokinetic modeling, to be approximately 1.7 times). Surprisingly, they have an equivalent AUC.
6) Surprisingly, the Cmax for IM injection is only about 55% of the Cmax for oral administration, but cetirizine showed up in blood stream much quicker: in only about 4 min for IM injection vs. in 20 min for oral administration. IM demonstrated a sustained release feature.

Example 2

Clinical Study of Reformulated Cetirizine Injection Given Via the IM Route

A disadvantage of the IM injection noted in the previous study was injection site pain. Benzyl alcohol was added to the IM injection to reduce injection site pain. Benzyl alcohol is a common preservative, and has been reported to have some local anesthetic effect. The objective of this study was to investigate the pharmacokinetics (PK) and the level of injection site pain of cetirizine injection at 10 mg dose diluted in saline containing 0.9% benzyl alcohol, administered by intramuscular injection using 1 inch needle in comparison to the use of 0.5 inch needle in healthy male and female volunteers after a single dose administration.

The study was a single center, randomized, single dose, laboratory-blinded, 2-period, 2-sequence, crossover design in healthy male and female subjects. The following treatments were to be administered under fasting conditions:
Treatment-A: 1.0 mL of Cetirizine HCl 10 mg/mL Injection+1.0 mL of Diluent* (intramuscular injection in the anterolateral thigh muscle slowly within a period of 0.5 minute using a 1 inch injection needle)
Treatment-B: 1.0 mL of Cetirizine HCl 10 mg/mL Injection+1.0 mL of Diluent* (intramuscular injection in the anterolateral thigh muscle slowly within a period of 0.5 minute using a 0.5 inch injection needle)
*Diluent: 0.9% bacteriostatic sodium chloride injection USP The treatments were to be administered to four (4) healthy male and female subjects. The PK parameters are given in the following Table:

| PARAMETER | TREATMENT-A (TEST) | | TREATMENT-B (TEST) | |
|---|---|---|---|---|
| | MEAN | C.V. (%) | MEAN | C.V. (%) |
| $C_{max}$ (ng/mL) | 160.98 | 20.1 | 166.11 | 16.2 |
| ln ($C_{max}$) | 5.0673 | 3.7 | 5.1035 | 3.0 |
| $T_{max}$ (hours) § | 2.25 | 20.2 | 3.00 | 20.1 |
| $AUC_T$ (ng · h/mL) | 1019.21 | 19.7 | 1049.51 | 15.7 |
| ln ($AUC_T$) | 6.9137 | 2.6 | 6.9473 | 2.2 |
| $AUC_\infty$ (ng · h/mL) | 2129.02 | 26.0 | 2140.83 | NC |
| ln ($AUC_\infty$) | 7.6387 | 3.7 | 7.6689 | NC |
| $AUC_{T/\infty}$ (%) | 50.79 | 18.3 | 59.95 | NC |
| $K_{el}$ (hours$^{-1}$) | 0.1056 | 30.4 | 0.1308 | NC |
| $T_{1/2el}$ (hours) | 6.99 | 30.1 | 5.30 | NC |
| $Cl_{TOT}/F$ (L/Hour) | 4.95 | 29.2 | 4.6700 | NC |
| $V_D/F$ (L) | 47.76 | 21.3 | 35.71 | NC |

Overall, the drugs tested were generally safe and well tolerated by human volunteers included in this study. In comparison to the Example 1 study results, at the same intramuscular 10 mg dose and 1 inch needle, where 79.2% of subjects (19 subjects) reported the adverse event injection site pain at intensity varying between mild and severe, in the present study where cetirizine injection was diluted in saline containing 0.9% benzyl alcohol, a lower incidence (50%; 2 subjects) of the adverse event injection site pain was reported where intensity varies between mild and moderate.

In addition to the reduction of injection site pain by the excipient benzyl alcohol, a surprising and unexpected reduction of Tmax was observed. The results show that the use of 1 inch needle for intramuscular injection of cetirizine solution provided a shorter $T_{max}$ of 2.25 hours compared to 3.00 hours when a 0.5 inch needle is used. In comparison to the study results from example 1, at the same intramuscular 10 mg dose and 1 inch needle, the addition of Saline containing 0.9% benzyl alcohol (1:1) has unexpectedly and surprisingly decreased the $T_{max}$ significantly from 4.00 hours (2.50-6.00 hours range) to 2.25 h (2.00-3.00 h range).

The improvement in Tmax upon the addition of benzyl alcohol to the formulation for intramuscular injection was completely unexpected.

The terms "a" and "an" do not denote a limitation of quantity, but rather denote the presence of at least one of the referenced item. The term "or" means "and/or." The terms "comprising," "having," "including," and "containing" are to be construed as open-ended terms (i.e., meaning "including, but not limited to"). Unless defined otherwise, technical and scientific terms used herein have the same meaning as is commonly understood by one of skill in the art to which this invention belongs. The endpoints of all ranges directed to the same component or property are inclusive and independently combinable.

The term "non-sedating antihistamines" represent the $2^{nd}$, $3^{rd}$ or later generations of antihistamines that are truly non-sedating and that are less-sedating than diphenhydramine.

The term "antihistamine" can also be expressed as "antagonist of the H1 receptor" or "H1 antihistamine".

The term "therapeutic equivalence" can also be expressed as "clinical equivalence", "clinically bioequivalent", or "clinical endpoint bioequivalence".

The term "equivalent" can also be expressed as "bioequivalent".

"Acute allergic reaction" means an allergic condition of the immediate type, generally occurring within minutes of contact with the material inducing the reaction. Acute allergic reactions are severe allergic reactions such as allergic reactions to blood or plasma, to food, to medications, or to other allergy inducing materials. "Acute allergic reaction" ranges from dermal issues including acute urticaria and angioedema to anaphylaxis. Anaphylaxis includes dermal issues as well as broncho-constriction (difficulty breathing) and hypotension. Symptoms of "acute allergic reaction" include acute urticaria, angioedema, erythema, wheezing, pruritus, constriction of airways, hypotension, or other issues of the immediate type, or combinations thereof. "Acute allergic reaction" differs from chronic or seasonal allergies (e.g., seasonal and/or perennial rhinitis, Chronic idiopathic urticaria). They are different on treatment regimens, patient types, source of allergens, patient population, medication usage, and etc. "Acute allergic reaction" does not include chronic allergies, seasonal allergies, seasonal rhinitis, perennial rhinitis, bronchitis, chronic urticaria, chronic idiopathic urticaria, or urticaria that is not acute urticaria.

The term "Cetirizine" is ($\pm$)-[2-[4-[(4-chlorophenyl)phenylmethyl]-1-piperazinyl]ethoxy] acetic acid and includes cetirizine itself, its pharmaceutical acceptable salts such as the HCl salt etc. and its various polymorphs. "Cetirizine" is a non-sedating antihistamine. Isomers of cetirizine such as levocetirizine and dextrocetirizine are referred to specifically herein, and it is intended that "cetirizine" alone is meant to refer to the ($\pm$) form, unless indicated otherwise.

The term "pharmaceutically acceptable salt" of a compound means any salt suitable for pharmaceutical use, for example, an acid-addition salt of a compound of the invention which is sufficiently basic, for example, an acid-addition salt with, for example, an inorganic or organic acid, for example hydrochloric, hydrobromic, nitric, methansulphonic, sulphuric, phosphoric, trifluoroacetic, para-toluene sulphonic, 2-mesitylen sulphonic, citric, acetic, tartaric, fumaric, lactic, succinic, malic, malonic, maleic, 1,2-ethanedisulphonic, adipic, aspartic, benzenesulphonic, benzoic, ethanesulphonic or nicotinic acid. In addition a suitable pharmaceutically acceptable salt of a compound of the invention, is, for example, a base-addition salt of a compound of the invention which is sufficiently acidic, for example, a metal salt, for example, sodium, potassium, calcium, magnesium, zinc or aluminum, an ammonium salt, a salt with an organic base which affords a physiologically acceptable cation, which includes quaternary ammonium hydroxides, for example methylamine, ethylamine, diethylamine, trimethylamine, tert-butylamine, triethylamine, dibenzylamine, N,N-dibenzylethylamine, cyclohexylethylamine, tris-(2-hydroxyethyl)amine, hydroxyethyl diethylamine, (1R,2S)-2-hydroxyinden-1-amine, morpholine, N-methylpiperidine, N-ethylpiperidine, piperazine, methylpiperazine, adamantylamine, choline hydroxide, tetrabutylammonium hydroxide, tris-(hydroxymethyl)methylamine hydroxide, L-arginine, N-methyl D-glucamine, lysine or arginine.

"Substantially free of hemolytic potential" means Hemolysis less than 10%, as discussed below under Hemolysis Studies. In some embodiments, it means less than 5%. In some other embodiments, it means less than 2%.

Embodiments of this invention are described herein, including the best mode known to the inventors for carrying out the invention. Variations of those preferred embodiments would become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of increasing peak plasma concentration and/or providing immediate onset of plasma concentration of cetirizine in an individual in need of treatment for acute urticaria or angioedema associated with an acute allergic reaction, comprising
administering to the individual an intravenous injection of an injectable cetirizine composition containing 2 mg to 20 mg of cetirizine at a rate of 10 mg per 1.0-1.5 minutes or faster,
wherein the peak plasma concentration (Cmax) of the intravenous injectable cetirizine composition is greater than twice the Cmax of a reference immediate-release oral cetirizine dosage form having the same number of mg of cetirizine as the injectable cetirizine composition, and wherein the area under the plasma time curve measured as $AUC_{0-36}$ hr and $AUC_{0-inf}$ is substantially the same for the intravenously injectable cetirizine composition and the reference immediate-release oral cetirizine dosage form.

2. The method of claim 1, wherein the peak plasma concentration (Cmax) of the intravenous injectable cetirizine composition is about 4.2 times that of the Cmax of the reference immediate-release oral cetirizine dosage form.

3. The method of claim 1, wherein administering the intravenous injection does not substantially increase the side effect of drowsiness compared to the reference immediate-release oral cetirizine dosage form.

4. The method of claim 1, wherein administering the intravenous injection does not substantially increase the side effect of dry mouth compared to the reference oral cetirizine dosage form.

5. The method of claim 1, wherein the mean Cmax for a 10 mg reference immediate-release oral cetirizine dosage form is about 318 ng/ml and the mean Cmax for a 10 mg injectable formulation via intravenous administration is about 1345 ng/ml hr.

6. The method of claim 1, wherein the mean $AUC_{0-36}$ for a 10 mg reference immediate-release oral cetirizine dosage form and a 10 mg injectable formulation via intravenous administration is about 2550-2640 ng/ml hr., and the mean $AUC_{0-INF}$ is about 2650-2772 ng/ml hr.

7. The method of claim 1, wherein the area under the plasma time curve for the injectable formulation via intravenous administration measured as $AUC_{0-1hr}$ is at about twice as large as the $AUC_{0-1hr}$ for a reference immediate-release oral cetirizine dosage form having the same number of mg of cetirizine as the injectable cetirizine composition.

8. The method of claim 1, wherein the area under the plasma time curve for the injectable formulation via intravenous administration measured as $AUC_{0-2hr}$ is at about 1.5 times as large as the $AUC_{0-2hr}$ for a reference immediate-release oral cetirizine dosage form having the same number of mg of cetirizine as the injectable cetirizine composition.

9. The method of claim 1, wherein the acute allergic reaction includes anaphylaxis.

10. The method of claim 1, wherein the injectable cetirizine composition contains 5 mg to 20 mg of cetirizine.

* * * * *